US011110306B2

(12) United States Patent
Montoya et al.

(10) Patent No.: US 11,110,306 B2
(45) Date of Patent: Sep. 7, 2021

(54) PORTABLE DEVICE FOR HEATING THE AIR THAT ENTERS THE NOSE OF A USER

(71) Applicants: Carlos Alberto Estrada Montoya, Medellin (CO); Esteban Betancur Valencia, Medellin (CO)

(72) Inventors: Carlos Alberto Estrada Montoya, Medellin (CO); Esteban Betancur Valencia, Medellin (CO)

(*) Notice: Subject to any disclaimer, the term of this patent is extended or adjusted under 35 U.S.C. 154(b) by 627 days.

(21) Appl. No.: 15/863,425

(22) Filed: Jan. 5, 2018

(65) Prior Publication Data
US 2019/0209873 A1    Jul. 11, 2019

(51) Int. Cl.
| A62B 9/00 | (2006.01) |
| A61M 16/10 | (2006.01) |
| A62B 18/02 | (2006.01) |
| A62B 18/08 | (2006.01) |
| A41D 3/00 | (2006.01) |

(52) U.S. Cl.
CPC ............. *A62B 9/003* (2013.01); *A41D 3/00* (2013.01); *A61M 16/1075* (2013.01); *A62B 18/025* (2013.01); *A62B 18/084* (2013.01); *A61M 2205/3368* (2013.01); *A61M 2205/3653* (2013.01); *A61M 2205/8206* (2013.01); *A61M 2205/8262* (2013.01); *A61M 2206/14* (2013.01)

(58) Field of Classification Search
CPC ......... A62B 9/003; A62B 9/04; A62B 18/003; A62B 18/025; A62B 18/084; A61M 16/0003; A61M 16/0666; A61M 16/0683; A61M 16/1075; A61M 2205/3368; A61M 2205/3653
See application file for complete search history.

(56) References Cited

U.S. PATENT DOCUMENTS

| 2,626,343 A * | 1/1953 | Fogel .................... H05B 3/342 |
| | | 219/211 |
| 2,784,714 A * | 3/1957 | Pitzipio .................. A62B 9/003 |
| | | 128/204.17 |
| 3,249,108 A * | 5/1966 | Terman .................. A61F 7/007 |
| | | 128/204.17 |
| 4,042,803 A * | 8/1977 | Bickford ................ H05B 3/342 |
| | | 219/211 |

(Continued)

OTHER PUBLICATIONS

"Outdoor N95 Intelligent Temperature Control Masks Anti-fog PM2.5 Dust Air Bacteria Pollen Cleaning Warm Electronic Electric Constant Temperature," Banggood.com, retrieved Jan. 5, 2018. <https://www.banggood.com/Outdoor-N95-Intelligent-Temperature-Control-Masks-Anti-fog-PM2_5-Dust-Air-Bacteria-Pollen-Cleaning-p-1128554.html>.

*Primary Examiner* — Kathryn E Ditmer
(74) *Attorney, Agent, or Firm* — BakerHostetler

(57) ABSTRACT

A portable device designed to heat the cold air that is inhaled through a person's nose is revealed, thus protecting respiratory function in adverse climates, especially for those suffering from lung diseases and the like, or for those who are susceptible or at risk of acquiring these diseases due to their age or work and need a protection mechanism. This device is composed of a support system and an energy system, wherein the support system guarantees the stability of the device next to the nose of the user, while the energy system heats the air that the user inhales through the nose and allows the user to regulate the temperature of the heat sink located near the nose by means of a control knob.

10 Claims, 6 Drawing Sheets

(56) References Cited

U.S. PATENT DOCUMENTS

| | | | | |
|---|---|---|---|---|
| 4,237,877 A * | 12/1980 | Boehler | ............... | A62B 18/006 128/203.29 |
| 4,305,388 A * | 12/1981 | Brisson | ............. | A61M 16/1075 128/203.27 |
| 4,564,748 A * | 1/1986 | Gupton | ............. | A61M 16/1075 219/497 |
| 4,620,537 A * | 11/1986 | Brown | ................. | A62B 18/025 128/201.13 |
| 4,793,343 A * | 12/1988 | Cummins, Jr. | ... | A61M 16/1075 128/203.27 |
| 4,905,686 A * | 3/1990 | Adams | ................. | A61M 16/06 128/204.17 |
| 5,008,517 A * | 4/1991 | Brekkestran | ........... | H05B 3/342 219/211 |
| 5,511,541 A * | 4/1996 | Dearstine | ............. | A62B 9/003 128/201.13 |
| 6,382,208 B2 * | 5/2002 | Reedy | ................... | A62B 9/003 128/204.17 |
| 6,430,935 B1 * | 8/2002 | Klett | ................. | B60H 1/00478 62/3.3 |
| 7,571,615 B1 * | 8/2009 | Bikes | ..................... | A42B 3/285 62/259.3 |
| 2001/0050079 A1 | 12/2001 | Piesinger | | |
| 2005/0284470 A1 * | 12/2005 | Wei | ..................... | A61M 16/107 128/200.14 |
| 2009/0000618 A1 * | 1/2009 | Warren | ............. | A61M 16/0677 128/202.13 |
| 2011/0041237 A1 * | 2/2011 | Gupta | ............... | A61M 16/0666 2/171.3 |
| 2012/0174922 A1 * | 7/2012 | Virr | ......................... | A62B 7/10 128/203.12 |
| 2012/0325227 A1 * | 12/2012 | Robinson | ............... | A24F 47/008 131/328 |
| 2013/0291859 A1 * | 11/2013 | Casey | ..................... | A61M 11/00 128/200.14 |
| 2014/0216459 A1 | 8/2014 | Vos et al. | | |
| 2015/0020801 A1 | 1/2015 | Frame et al. | | |
| 2015/0114389 A1 * | 4/2015 | Sernfalt | ................ | A62B 9/003 128/202.22 |
| 2015/0136129 A1 * | 5/2015 | Mahadevan | ...... | A61M 16/0069 128/203.14 |
| 2016/0008566 A1 * | 1/2016 | Partington | ........ | A61M 16/0875 128/201.13 |
| 2017/0245567 A1 * | 8/2017 | Fathollahi | ............... | H02J 7/342 |
| 2019/0009114 A1 * | 1/2019 | Han | ..................... | A62B 18/003 |

* cited by examiner

PORTABLE DEVICE FOR HEATING THE AIR THAT ENTERS THE NOSE OF A USER

FIELD OF THE INVENTION

The present invention belongs to the field of medical and/or protection devices that have electrical and electronic elements for their operation, since it consists of a portable device that has a heat sink stably located near the nose of the user to heat the air inhaled, and that also has a control board and other elements that allow regulating the energy transferred by the heat sink to the air inhaled by the user. In this way, the disclosed device favors the respiratory function of people suffering from lung and similar conditions or who need protection against adverse weather conditions.

BACKGROUND OF THE INVENTION

It is a known fact that climate has a marked impact on the health of people, so that, for example, while a very hot climate can cause some health problems such as dehydration, the cold conditions intensify respiratory diseases.

These health effects are more severe when a person does not live regularly, or is not accustomed to living, in hot or cold weather conditions, but for work or personal reasons has to relocate to this type of area on a temporary or permanent basis.

However, these conditions are also suffered by people who, while living regularly in the area where adverse conditions are present, are forced to face them for work or routine reasons. Thus, for example, older people in a strong winter, workers in maritime equipment, oil exploration or scientific research, as well as personnel belonging to security forces, are forced to expose themselves to very difficult conditions in the zones they inhabit.

Now, in particular reference to cold weather conditions, it is common to find that one of the effects that most people suffer in areas or sites characterized by low temperatures is influenza or flu (the above because the responsible viruses spread more easily in cold climates).

However, prolonged exposure to cold air, and particularly the inhalation of cold air, also promotes the appearance and exacerbation of other types of respiratory diseases, including asthma, bronchitis, CPOD (chronic obstructive pulmonary disease) and pulmonary emphysema, since when a person breathes in cold air, the respiratory tubes contract, hindering the flow of air. Likewise, the constant breathing of cold air can lead to frequent constriction of the lungs, which can contribute to premature aging of the lungs.

Due to the fact that the exposure to cold air, and particularly the inhalation of cold air, triggers the appearance of pulmonary affections or aggravates existing illnesses, the need to establish basic care with the aim of protecting oneself from such effects is well known. In this sense, it is normal to hear that babies, children, the elderly and people suffering from lung diseases should take special care when going out in cold weather, going on vacation to a cold area or when thinking about changing residence to a colder place than the previous one.

Regarding the above, there are several preventive measures that are usually suggested, including covering the nose and mouth when the person is outdoors, and the use of bronchodilators to clear the airways. It is also recommended to always breathe through the nose, and never through the mouth.

Unfortunately, these measures are usually unsuccessful or insufficient to prevent the inhalation of cold air to generate or intensify different types of pulmonary conditions, a fact that has implied the need to think of measures and mechanisms of greater complexity to mitigate and, if possible, avoid such adverse effects.

Thus, for example, patent document US2015/0020801 (Breathing assistance apparatus with serviceability features) discloses a respiratory assistance apparatus that provides a flow of humidified and hot air to the user. This apparatus comprises a flow generator, a humidifying chamber and a conduit connected to the flow generator, a user breathing interface connected to the conduit and a display screen adapted to provide visual information to the user.

In turn, document US2014/0216459 (Wire heated tube with temperature control system for humidifier for respiratory apparatus) discloses a detection circuit for a heating conduit for use in a respiratory apparatus, which contemplates the use of a temperature control.

On the other hand, patent document US2001/0050079 (Personal powered air filtration, sterilization, and conditioning system) refers to a personal and portable system for filtering air that comprises a device through which filtered air flows into the system that is in a belt. The device disclosed therein additionally contemplates mechanisms for heating the filtered air through the use of a resistance with an automatic control.

In the market there are also known devices designed to counteract the problems generated by breathing cold air. So, for example, the device called "Outdoor N95 Intelligent Temperature Control Masks" (https://www.banggood.com/Outdoor-N95-Intelligent-Temperature-Control-Masks-Anti-fog-PM2_5-Dust-Air-Bacteria-Pollen-Cleaning-p-1128554.html) basically consists of a mask comprising a filter and a heating system of the surrounding air using a rechargeable battery located inside the mask and lasting about an hour.

Taking into account the teachings of the state of the art, including the type of configurations proposed to favor the conditions of the air surrounding the nose of a user, it is clear that the need for developing a new device that allows heating in a regulated manner the air inhaled by a user, but that also has an optimized design so that said user feels the comfort of using it for long periods of time, thus, limiting as much as possible respiratory system disorders, or worse, the intensification of existing diseases, persisted in the state of the art.

General Description of the Invention

Taking into account the need for having an apparatus whose design, ergonomics and functionality renders it easy for users to use it permanently during their stay in areas with cold air, the applicant of the invention developed a portable device that heats the air that is inhaled through the nose of the user at a temperature regulated by the user himself. Said device is provided with a support system particularly developed to offer the user the possibility of using it for long periods of time without being uncomfortable in the parallel development of other activities.

The operation of the device disclosed herein is based on its energy system, which consists basically of the following elements: An external battery that acts as the source of energy of the device, a resistance responsible for converting the electrical energy supplied into heat, a heat sink designed to optimally conduct the heat from the resistance to the air that is going to be inhaled, a temperature sensor (for example a thermocouple, a thermistor or a resistance temperature detector) which allows determining the temperature of the heatsink and the air that surrounds it, an adjustment knob by means of which the user regulates the desired temperature and a control board in charge of regulating the passage of current from the external battery to the resistance depending on the information coming from the adjustment knob and the temperature sensor.

In turn, the device additionally includes a support system in charge of giving stability to the device and at the same time allowing it to adapt to the user in a comfortable and minimally invasive manner. Said support system consists basically of the following elements: A flexible and adjustable hose responsible for covering the cables of the resistance and the temperature sensor and at the same time to fix in an adjustable manner the heat sink at the position desired by the user, and a support for the ears that allows fixing the device to the head of the user.

As a result of the design and operation characteristics developed by the applicant, the device disclosed herein turns out to be an effective device for limiting the negative effects on health that the cold air intake generates in those subjects who are exposed to cold climate zones, especially when said people suffer from problems in their respiratory system.

DETAILED DESCRIPTION OF THE INVENTION

Figure 1:
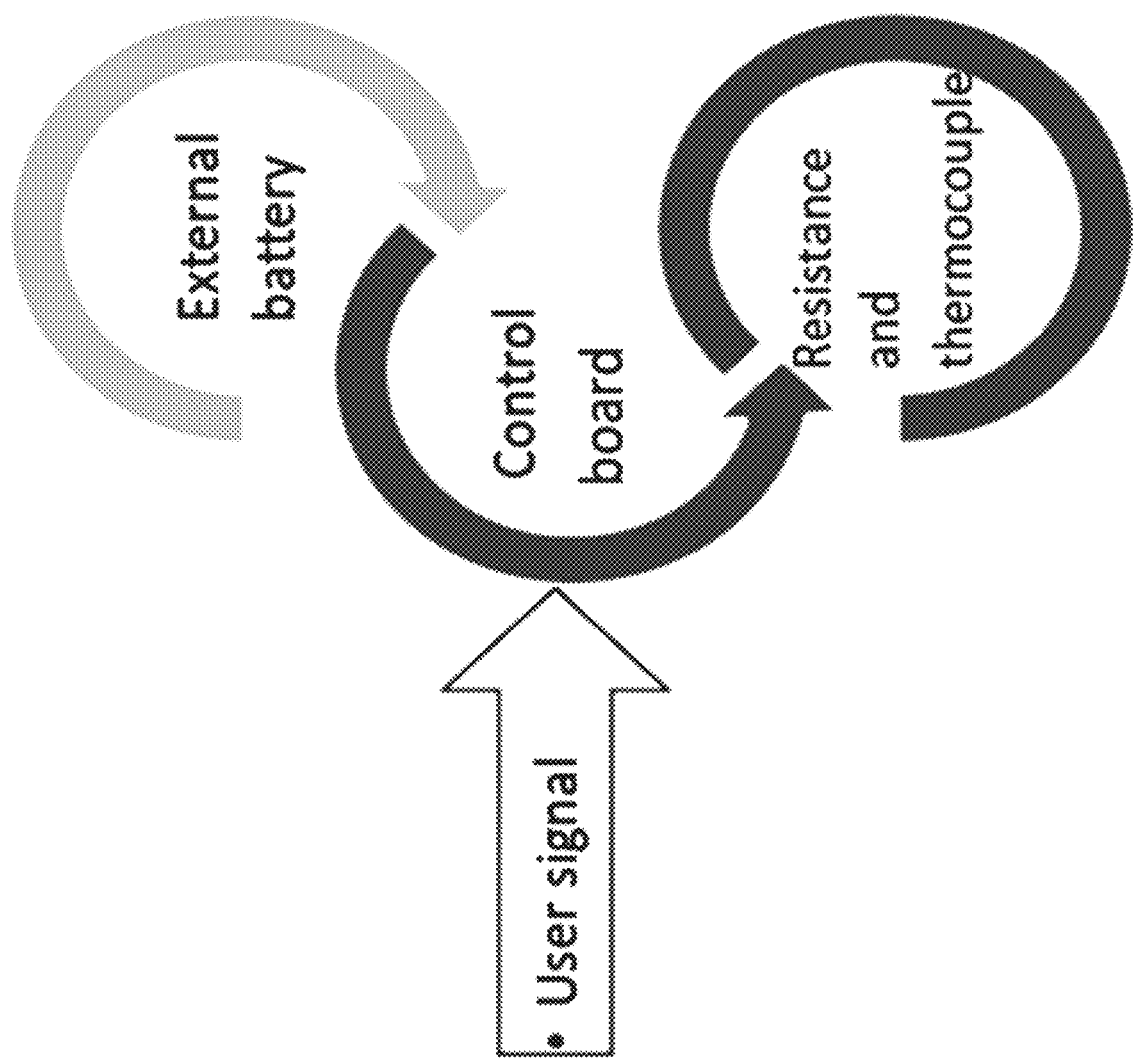
FIG. 1 is a flow diagram of the energy system that is part of the developed device and that allows heating in a controlled manner the air that enters through the nose of the user.

In accordance with FIG. 1, the device disclosed herein allows to heat in a controlled manner the air entering the nose of the user as a result of the following operating mechanism:

A power source (such as an external battery) is responsible for providing electrical power to the device. In turn, an electrical resistance receives the energy coming from said energy source and transforms it into heat, which is in turn transmitted to the surrounding air by means of the heat sink. On the other hand, a temperature sensor (such as a thermocouple) is located very close to the electrical resistance to constantly measure the temperature of the heat sink and the air that is heated. Finally, an electronic control board allows regulating the flow of energy or electrical power from the power source to the electrical resistance, wherein said flow and power are determined by the temperature that the user establishes as desired through a control knob located on the external part of the electronic control board, and likewise are determined by the information that said board receives from the temperature sensor.

This temperature and power are within pre-established limits and determined by the applicant to oscillate within a range that does not cause harm to human beings, and that are absolutely tolerable by the respiratory system without exceeding at any time the maximum admissible temperature for the human being.

Figure 2:
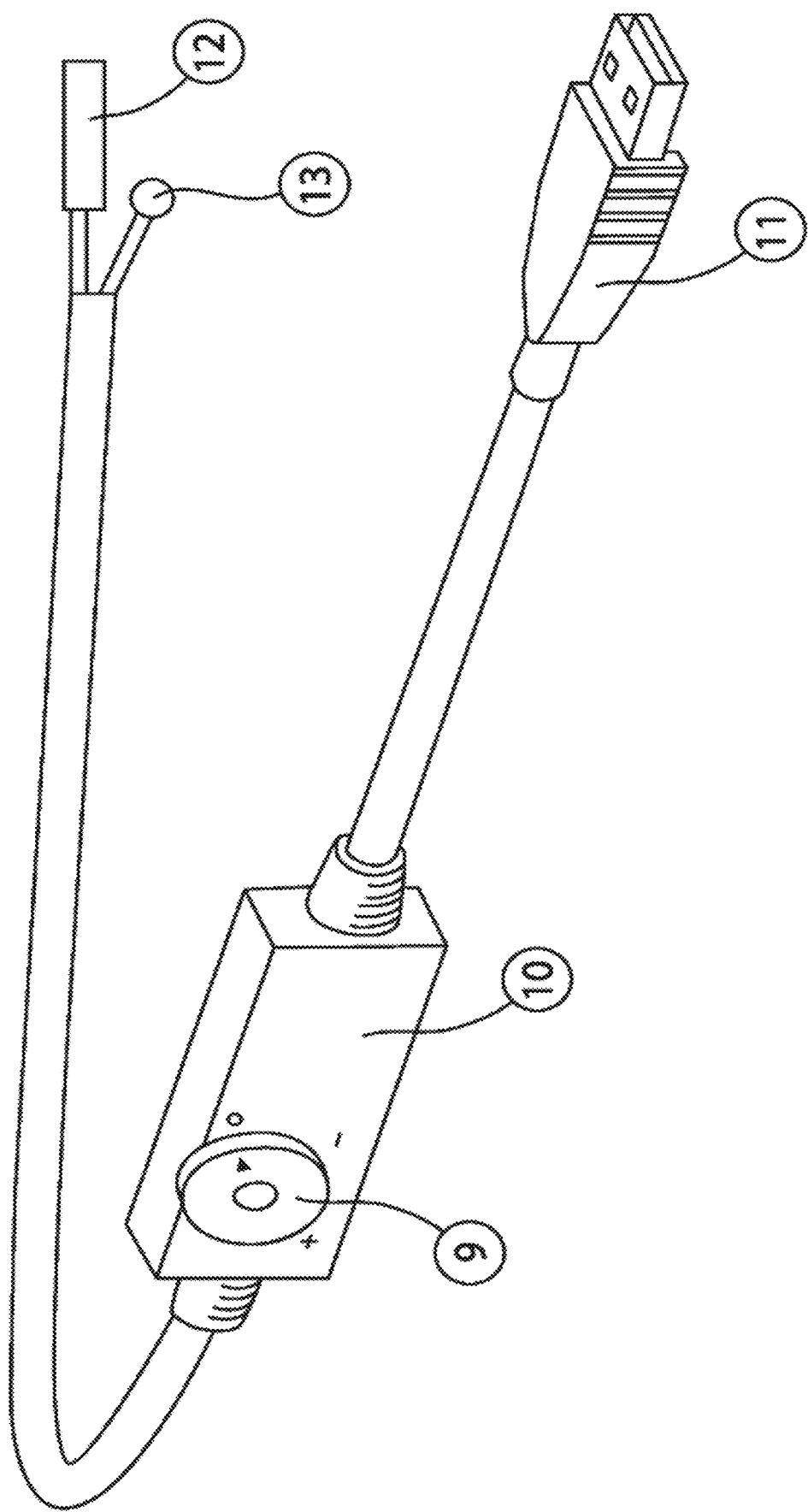
FIG. 2 shows in detail the elements that make up the energy system of the device revealed here.

In a preferred embodiment and according to FIG. 2, the operation of the device disclosed herein is based on an energy system consisting of a control board (10) connected by means of a USB cable (11) to an external source of power, and at the same time it is connected to an electrical resistance (12) and to a thermistor with glass encapsulation which acts as a temperature sensor (13).

Said control board (10) is housed inside a housing that covers it. However, a temperature control knob (9) which is connected to the control board (10) is located outside said cover casing in order to allow the user to adjust the temperature depending on the climate or his particular health conditions.

In a particular embodiment of the invention, the energy source of the device consists of an external battery with a USB port (5 Volts) of 2.1 amperes of current, so that the power necessary for the correct operation of the device can be guaranteed.

In another particular embodiment of the invention, the electrical resistance (12) and the temperature sensor (13) are connected to the control board (10) by means of electric cables covered with a flexible tube to allow its maneuverability, but manufactured in a suitable material to provide stability and support to these elements.

Ideally, said flexible tube consists of a plastic hose with a minimum internal diameter of 5 mm to be able to incorporate the cables of the electrical resistance (12) and the temperature sensor (13). The dimensions of the hose address both the dimensions of the necessary cables and the comfort of this part on the user's face.

In another particular embodiment of the invention, the electrical resistance (12) is 40 Watts, although under normal conditions of use of the device said resistance will operate up to a maximum of 10 Watts.

Figure 3:
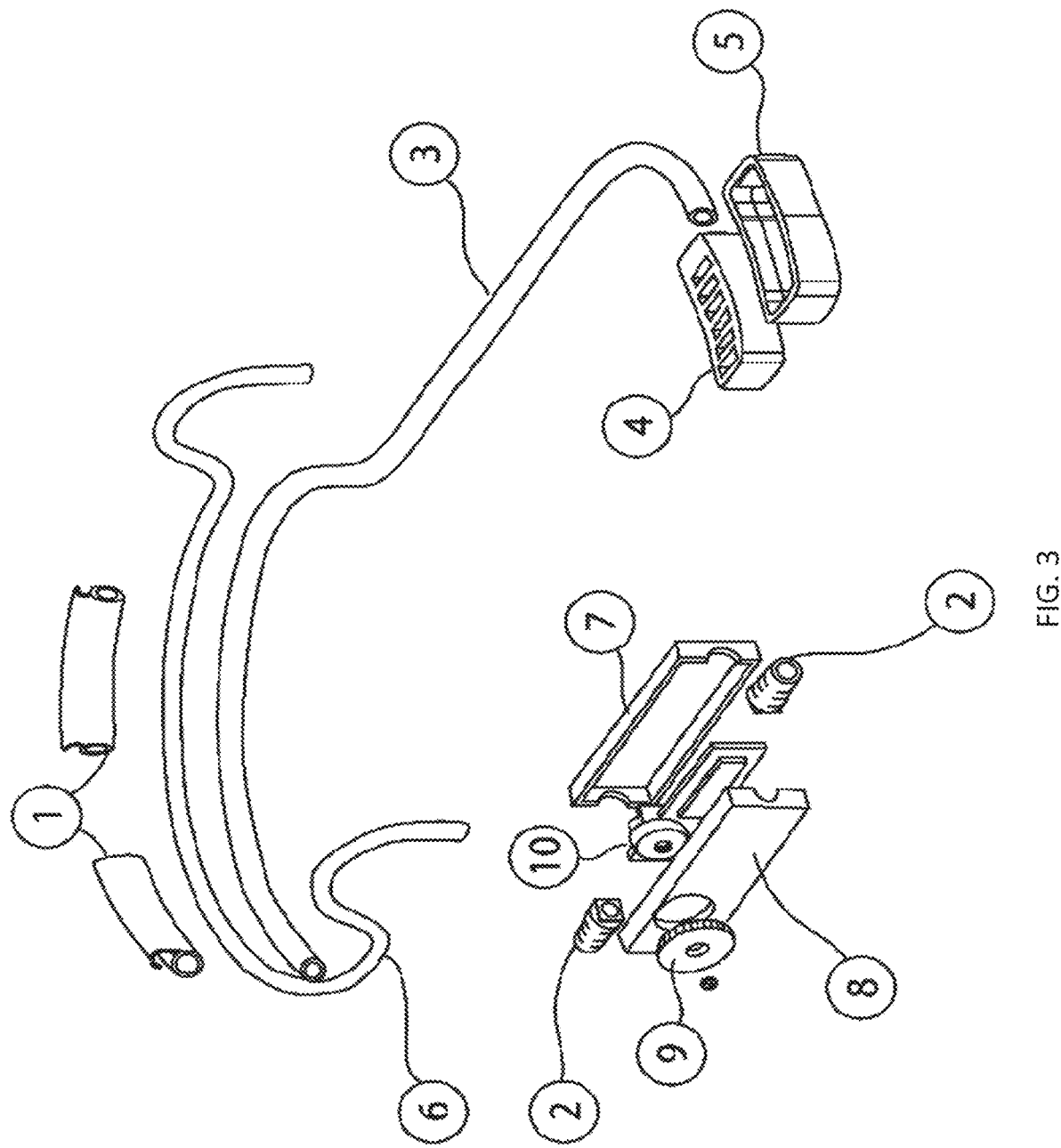
FIG. 3 corresponds to the exploded view of the device, including the energy system and the support system.

Now, referring to FIG. 3, the device disclosed herein additionally comprises a support system in charge of giving stability to the device and at the same time allowing it to be accommodated to the user in a comfortable and minimally invasive manner Said support system is composed of two main elements: the ears support (6), which is designed to be fixed to the user's head and give stability to the device, and the flexible hose (3) that apart from covering the cables of the electrical resistance (12) and the temperature sensor (13), is responsible for fixing said elements (12) and (13) in the position desired by the user of the device.

To fulfill its function, said ear support (6) must have the necessary flexibility to generate comfort in the user, but at the same time must have sufficient rigidity to support all the components of the device.

According to the above and in a particular embodiment of the invention, said ear support (6) is made of shape memory wire or plastic with a rubber coating for aesthetic and ergonomic reasons.

The support system of the device disclosed herein additionally comprises a series of supports (1) and joining links (2) that allow the correct assembly of all the elements that make up the device.

In another embodiment of the invention, the electrical resistance (12) and the temperature sensor (13) are housed inside a heatsink (4), which basically consists of a housing with vertical grooves to allow cold air to enter through the lower face, be heated by the energy transferred from the electrical resistance (12), come out through the upper face and finally be inhaled through the nose of the user.

In a further embodiment of the invention, said heat sink (4) is surrounded by a liner (5) to prevent a burn as a result of direct contact between the heatsink (4) and the user's skin.

The lining (5) surrounding the heat sink (4) can be made of any material that acts as a thermal insulator. In a preferred embodiment of the invention, said lining (5) will consist of a silicone lining that can additionally incorporate a windbreak tab.

Figure 4:
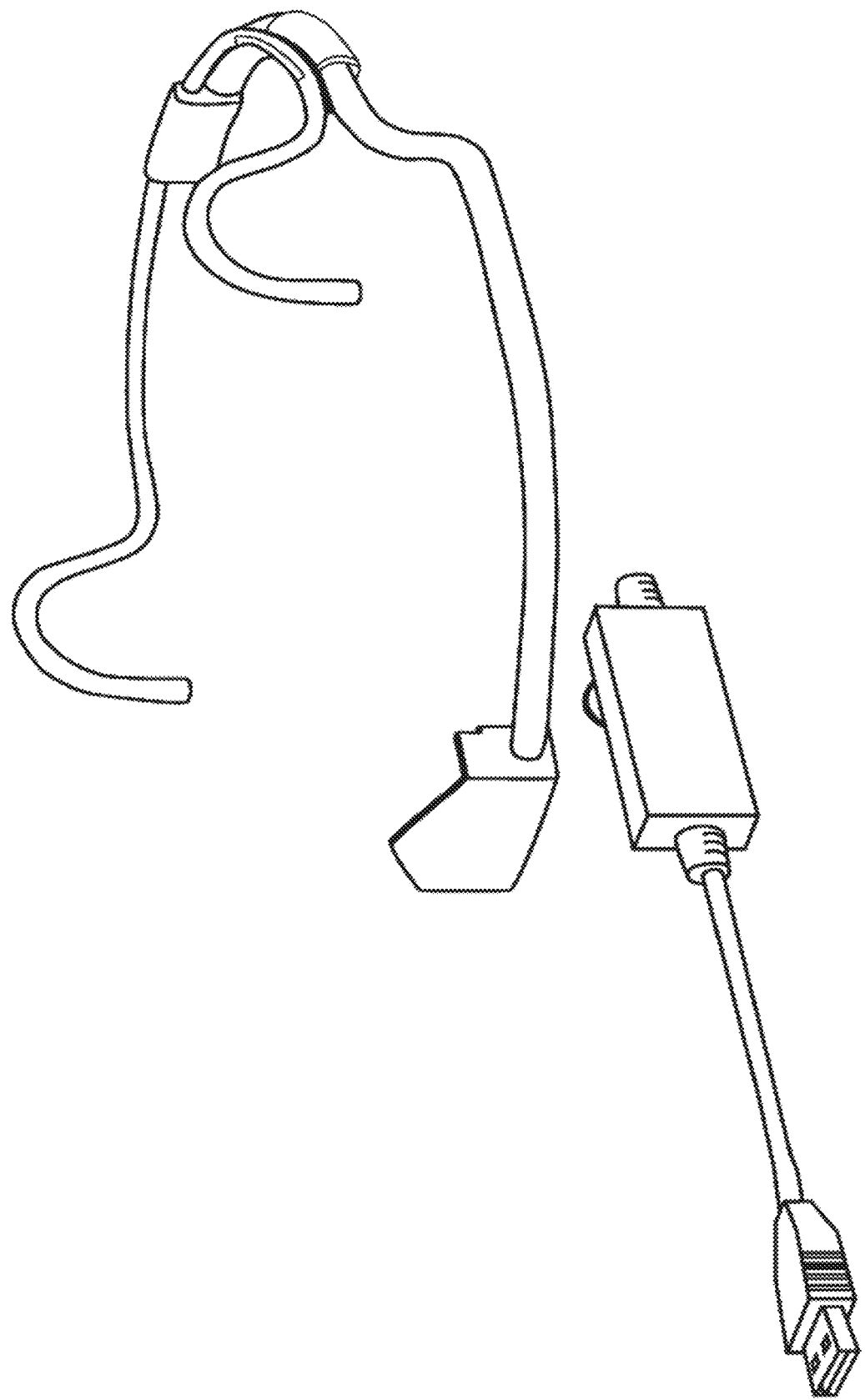
FIG. 4 shows a preferred embodiment of the disclosed device, as would be appreciated by the user.

In FIG. 4, the energy and support systems that make up the device of the present invention completely assembled are shown separately.

Figure 5:
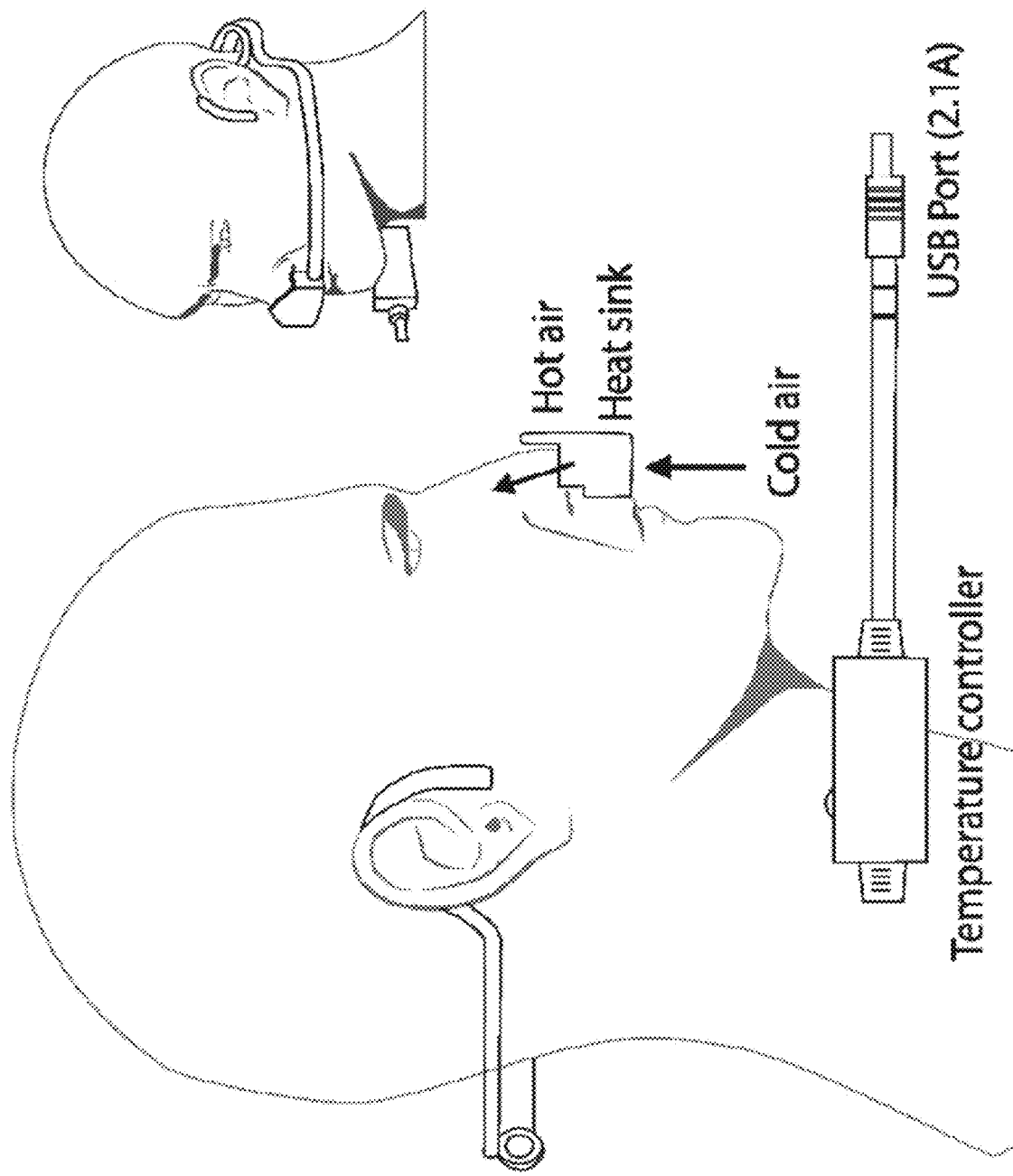
FIG. 5 details the location of the device revealed in a user's head.

In turn, FIG. 5 shows a particular mode of the location of the device revealed here in the head of a user, observing how said design turns out to be ergonomic and minimally invasive and therefore encourages its use for long periods of time.

Figure 6:
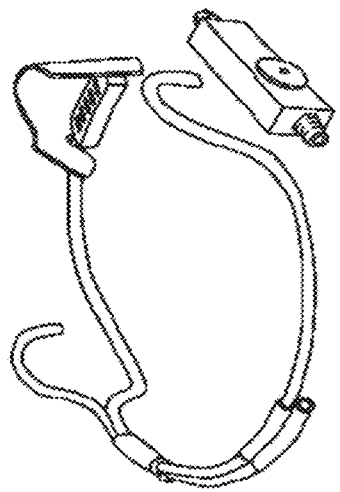
FIG. 6 details the device in a user's head including a wind protection accessory.
Figure 6:
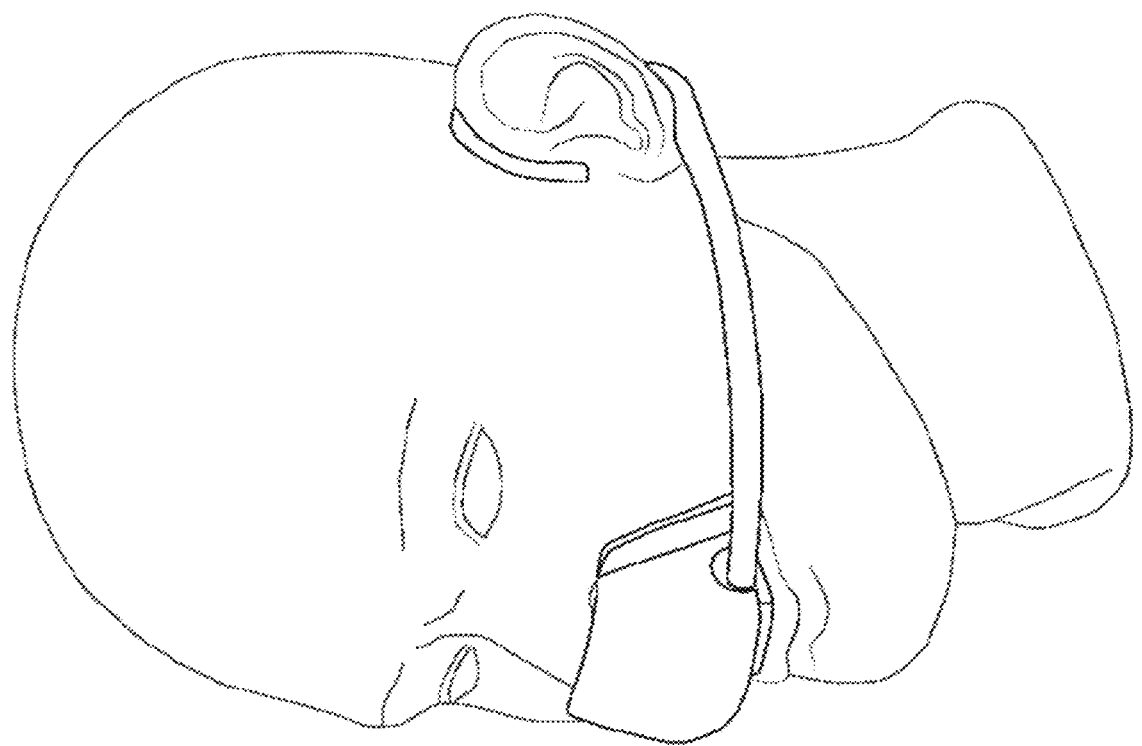

In another embodiment of the invention, and in accordance with FIG. 6, the disclosed device includes a windproof accessory or partial mask to improve its efficiency in conditions of strong wind or very low temperatures. This accessory generates a confined environment around the nose and mouth with warm air for breathing. This accessory renders compatible the simultaneous use of the device with extreme cold protective textile garments such as scarves, jackets and sweaters with high collars.

Thanks to the design of the developed device, its use does not affect in any way the use of traditional protection accessories, such as scarves, clothing with high collars, among others.

EXAMPLE

The amount of air inhaled by a human being is around 6 L/min (Liters per minute) for a person at rest and 90 L/min for a person exercising.

To increase 10° C. (Celsius degrees) the temperature of the air inhaled by a person with an average breathing rate of 30 L/min, it is calculated, according to the specific heat of the air and a system efficiency of 80%, a necessary power of 8.1 W (Watts).

This power must be dissipated in the form of heat by the heat sink, which means that it will increase its temperature and deliver energy to the air, in a way proportional to its surface area and convection coefficient. It is calculated, for a heat sink with a surface area of 18.9 $cm^2$ and an average convection coefficient of 85 $W/m^2$-° C. (Watts per square meter and Celsius degree), which will reach on average 50° C. over the ambient temperature to dissipate the heat.

Therefore, a control system is included that regulates and maintains the temperature of the heatsink around a safe range that promotes the necessary heating of the air.

The nominal power consumption of 8.1 W ensures that a battery or power source with a USB port is capable of supplying the necessary power and lasts considerable periods of time. A single Lithium Ion battery (reference 18650) would deliver the necessary power for the device for approximately 1.2 hours of continuous use.

In turn, the head restraint system guarantees an ergonomic design for the user, since the design of the headband has been defined based on statistical anthropometric measurements of the population of interest. According to these statistical data, a distance between the ears of 15 cm and different parameters for the measurement of the ears, guarantee the comfort in the adjustment for 80% of the potential users.

According to the above, the device disclosed herein, designed to heat the cold air that is inhaked through a person's nose, corresponds to a useful device to improve the respiratory function of those who may be affected when they are located in areas of cold weather. Said beneficial effect on the health of the user is further increased thanks to the particular design of the device increasing the level of acceptance of the user to use it permanently, if so required.

Finally, and although the device disclosed herein has been disclosed in detail for illustrative purposes, it will be recognized that minor variations or modifications made thereto are within the scope of the present invention.

Additionally, it is clarified that the terms in which this description has been written should always be taken in a broad and non-limiting sense.

The invention claimed is:

1. A portable device for heating air that enters a nose of a user, wherein the portable device is formed by an energy system and a support system;
where said energy system comprises in turn an external source of energy, an electronic control board, an electrical resistance, a heat sink, a temperature sensor and a temperature control knob, the heat sink having a plurality of vertical grooves and a continuous annular lining around the heat sink as a thermal insulator, the plurality of vertical grooves extending from a lower face of the heat sink to an upper face of the heat sink, the plurality of vertical grooves allowing air to enter through the lower face and to come out through the upper face, wherein the electrical resistance and the temperature sensor are both housed inside the heat sink such that heat produced by the electrical resistance is transferrable to air within the grooves of the heat sink, which is inhalable through the nose of the user when coming out through the upper face of the heat sink;
and wherein said support system comprises a plurality of couplings and a hose that connect the elements of the energy system together and at the same time allow the portable device to be fixed to the user.

2. The portable device of claim 1, wherein the electronic control board is connected to the external source of energy, to the temperature control knob, to the electrical resistance and to the temperature sensor, in such a way as to allow it to regulate a flow of electrical energy from the external source of energy to the electrical resistance depending on information received from the temperature control knob and the temperature sensor.

3. The portable device of claim 1, wherein the external source of energy is a portable battery that is connected to the electronic control board via a USB cable.

4. The portable device of claim 3, wherein said portable battery is configured to delivers 5 Volts and 2.1 Amperes.

5. The portable device of claim 1, wherein the temperature sensor is a thermistor with glass coating.

6. The portable device of claim 1, wherein the plurality of couplings and the hose form an ear support by which said device is fixed to the head of the user.

7. The portable device of claim 1, wherein the plurality of couplings and the hose cover cables that connect the electronic control board with the electrical resistance and the temperature sensor, and allow the user to adjust the position of the heat sink relative to his nose.

8. The portable device of claim 1, which additionally comprises a windbreaker or partial mask that is configured to covers the nose and/or mouth of the user.

9. The portable device of claim 1,
wherein the electronic control board is connected to the external source of energy, to the temperature control knob, to the electrical resistance and to the temperature sensor, in such a way as to allow it to regulate a flow of electrical energy from the external source of energy to the electrical resistance depending on information received from the temperature control knob and the temperature sensor; and
wherein the external source of energy is a portable battery that is connected to the electronic control board via a USB cable.

10. The portable device of claim 1,
wherein the electronic control board is connected to the external source of energy, to the temperature control knob, to the electrical resistance and to the temperature sensor, in such a way as to allow it to regulate a flow of electrical energy from the external source of energy to the electrical resistance depending on information received from the temperature control knob and the temperature sensor; and
wherein the temperature sensor is a thermistor with glass coating.

* * * * *